(12) United States Patent
Kang et al.

(10) Patent No.: US 6,596,500 B1
(45) Date of Patent: Jul. 22, 2003

(54) BINDING OF RETINOIDS TO M6P/IGF-II RECEPTOR

(75) Inventors: Jing X. Kang, North Andover, MA (US); Alexander Leaf, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/207,363

(22) Filed: Dec. 8, 1998

(51) Int. Cl.[7] ..................... G01N 33/53; G01N 33/574; C12N 15/63; C12Q 1/00; A01N 63/00
(52) U.S. Cl. ..................... 435/7.2; 435/4; 435/7.21; 435/7.23; 435/455; 435/325; 424/93.1; 424/93.2; 424/93.21
(58) Field of Search ..................... 435/4, 7.2, 7.21, 435/7.23, 455, 375, 377, 325; 424/93.1, 93.2, 93.21; 514/725

(56) References Cited

U.S. PATENT DOCUMENTS 5,658,949 A * 8/1997 Aggarwal ................ 514/557
5,824,685 A * 10/1998 Campochiaro et al. ..... 514/277

OTHER PUBLICATIONS

Kang et al., Proc. Nat. Acad. Sci., 10:13687–13691, 1998.*
Kang et al., Proc. Natl. Acad. Sci., 9:13671–13676, 1997.*
Verma et al., Nature, 389:239–242, 1997.*
F. Ledley, Pharmaceutical Research, 13:1595–1614, 1996.*
J. Olson, in "Handbook of Vitamins, Nutritional, Biochemical, and Clinical Aspects", ed. L.J. Machlin, Marcel Dekker, Inc., NY, Chapter 1, pp. 1–6, 1984.*
Orkin et al., in "Report And Recommendations Of The Panel To Assess The NIH Investment In Research On Gene Therapy", pp. 1–41, Dec. 7, 1995.*
Ahuja et al., "Rescue of the Limb Deformity in Hammertoe Mutant Mice by Retinoic Acid–Induced Cell Death", Developmental Dynamics 208:466–481, 1997.
Chambon, "A Decade of Molecular Biology of Retinoic Acid Receptors", Faseb J. 10:940–954, 1996.
De Luca, "Retinoids and Their Receptors in Differentiation, Embryogenesis, and Neoplasia", Faseb J. 5:2924–2933, 1991.
De Souza et al., "M6P/IGF2R Gene is Mutated in Human Hepatocellular Carcinomas With Loss of Heterozygosity", Nature Genetics 11:447–449, 1995.
Dennis et al., "Cellular Activation of Latent Transforming Growth Factor β Requires Binding to the Cation–Independent Mannose 6–phosphate/insulin–like . . . ", Proc. Natl. Acad. Sci. USA 88:580–584, 1991.
Delia et al., "N–(4–Hydroxyphenyl)retinamide Induces Apoptosis of Malignant Hemopoietic Cell Lines Including Those Unresponsive to Retinoic Acid", Cancer Research 53:6036/6041, 1993.
Hankins et al., "M6P/IGF2 Receptor: A Candidate Breast Tumor Suppressor Gene", Oncogene 12:2003–2009, 1996.
Kiess et al., "Biochemical Evidence That the Type II Insulin– like Growth Factor Receptor Is Identical to the Cation–independent Mannose 6–Phosphate Receptor", The Journal of Biological Chemistry 263:9339–9344, 1988.
Kornfeld, "Structure and Function of the Mannose 6–Phosphate/Insulin Like Growth Factor II Receptors", Ann. Rev. Biochem. 61:307–330, 1992.
MacDonald et al, "A Single Receptor Binds Both Insulin–Like Growth Factor II and Mannose–6–Phosphate", Science 239:1134–1137, 1988.
Mangelsdorf et al., "The RXR Heterodimers and Orphan Receptors", Cell 83:841–850, 1995.
Morgan et al., "Insulin–like Growth Factor II Receptor as a Multifunctional Binding Protein", Nature 329:301–307, 1987.
Nissley et al., "Developmental Expression of the IGF–II/Mannose 6–Phosphate Receptor", Molecular Reproduction and Development 35:408–413, 1993.
O'Connell et al., "Retro–Retinoids in Regulated Cell Growth and Death", J. Exp. Med. 184:549–555, 1996.
Oka et al., "Direct Demonstration of Rapid Insulin–like Growth Factor II Receptor Internalization and Recycling in Rat Adipocytes", The Journal of Biological Chemistry 260:9435–9442, 1985.
Pfahl, "Vertebrate Receptors: Molecular Biology, Dimerization and Response Elements", Cell Biology 5:95–103, 1994.
Sun et al., "Differential Effects of Synthetic Nuclear Retinoid Receptor–selective Retinoids on the Growth of Human Non–Small Cell Lung Carcinoma Cells", Cancer Research 57:4931–4939, 1997.
Wang et al., "Deficient Transforming Growth Factor–β1 Activation and Excessive Insulin–like Growth Factor II (IGFII) Expression in IGFII Receptor–Mutant Tumors", Cancer Research 57:2543–2546, 1997.

* cited by examiner

Primary Examiner—Shin-Lin Chen
(74) Attorney, Agent, or Firm—Fish & Richardson P.C.

(57) ABSTRACT

Disclosed are methods for inhibiting proliferation of a cell or inducing apoptosis. In general, the methods include the steps of providing an elevated level of M6P/IGF2R protein in the cell, and contacting the cell with a compound, e.g., a retinoid, that binds to the M6P/IGF2R protein. The methods can be used to inhibit proliferation of a cancer cell or induce apoptosis in a cancer cell. Also disclosed is a method for potentiating an M6P/IGF2R-mediated effect in a cell. Also disclosed are screening methods for identification of compounds that bind directly to the retinoic acid binding site of a M6P/IGF2R protein.

24 Claims, 5 Drawing Sheets

SEQUENCE LISTING

```
<160> NUMBER OF SEQ ID NOS: 1

<210> SEQ ID NO 1
<211> LENGTH: 2491
<212> TYPE: PRT
<213> ORGANISM: Homo sapiens

<400> SEQUENCE: 1

Met Gly Ala Ala Ala Gly Arg Ser Pro His Leu Gly Pro Ala Pro Ala
 1               5                  10                  15

Arg Arg Pro Gln Arg Ser Leu Leu Leu Gln Leu Leu Leu Leu Leu Val
                20                  25                  30

Ala Ala Pro Gly Ser Thr Gln Ala Gln Ala Ala Pro Phe Pro Glu Leu
            35                  40                  45

Cys Ser Tyr Thr Trp Glu Ala Val Asp Thr Lys Asn Asn Val Leu Tyr
        50                  55                  60
```

-continued

```
Lys Ile Asn Ile Cys Gly Ser Val Asp Ile Val Gln Cys Gly Pro Ser
 65                  70                  75                  80

Ser Ala Val Cys Met His Asp Leu Lys Thr Arg Thr Tyr His Ser Val
                 85                  90                  95

Gly Asp Ser Val Leu Arg Ser Ala Thr Arg Ser Leu Leu Glu Phe Asn
                100                 105                 110

Thr Thr Val Ser Cys Asp Gln Gln Gly Thr Asn His Arg Val Gln Ser
            115                 120                 125

Ser Ile Ala Phe Leu Cys Gly Lys Thr Leu Gly Thr Pro Glu Phe Val
130                 135                 140

Thr Ala Thr Glu Cys Val His Tyr Phe Glu Trp Arg Thr Thr Ala Ala
145                 150                 155                 160

Cys Lys Lys Asp Ile Phe Lys Ala Asn Lys Glu Val Pro Cys Tyr Val
                165                 170                 175

Phe Asp Glu Glu Leu Arg Lys His Asp Leu Asn Pro Leu Ile Lys Leu
                180                 185                 190

Ser Gly Ala Tyr Leu Val Asp Asp Ser Asp Pro Asp Thr Ser Leu Phe
                195                 200                 205

Ile Asn Val Cys Arg Asp Ile Asp Thr Leu Arg Asp Pro Gly Ser Gln
210                 215                 220

Leu Arg Ala Cys Pro Pro Gly Thr Ala Ala Cys Leu Val Arg Gly His
225                 230                 235                 240

Gln Ala Phe Asp Val Gly Gln Pro Arg Asp Gly Leu Lys Leu Val Arg
                245                 250                 255

Lys Asp Arg Leu Val Leu Ser Tyr Val Arg Glu Glu Ala Gly Lys Leu
                260                 265                 270

Asp Phe Cys Asp Gly His Ser Pro Ala Val Thr Ile Thr Phe Val Cys
            275                 280                 285

Pro Ser Glu Arg Arg Glu Gly Thr Ile Pro Lys Leu Thr Ala Lys Ser
            290                 295                 300

Asn Cys Arg Tyr Glu Ile Glu Trp Ile Thr Glu Tyr Ala Cys His Arg
305                 310                 315                 320

Asp Tyr Leu Glu Ser Lys Thr Cys Ser Leu Ser Gly Glu Gln Gln Asp
                325                 330                 335

Val Ser Ile Asp Leu Thr Pro Leu Ala Gln Ser Gly Gly Ser Ser Tyr
                340                 345                 350

Ile Ser Asp Gly Lys Glu Tyr Leu Phe Tyr Leu Asn Val Cys Gly Glu
            355                 360                 365

Thr Glu Ile Gln Phe Cys Asn Lys Lys Gln Ala Ala Val Cys Gln Val
    370                 375                 380

Lys Lys Ser Asp Thr Ser Gln Val Lys Ala Ala Gly Arg Tyr His Asn
385                 390                 395                 400

Gln Thr Leu Arg Tyr Ser Asp Gly Asp Leu Thr Leu Ile Tyr Phe Gly
                405                 410                 415

Gly Asp Glu Cys Ser Ser Gly Phe Gln Arg Met Ser Val Ile Asn Phe
            420                 425                 430

Glu Cys Asn Lys Thr Ala Gly Asn Asp Gly Lys Gly Thr Pro Val Phe
            435                 440                 445

Thr Gly Glu Val Asp Cys Thr Tyr Phe Phe Thr Trp Asp Thr Glu Tyr
            450                 455                 460

Ala Cys Val Lys Glu Lys Glu Asp Leu Leu Cys Gly Ala Thr Asp Gly
465                 470                 475                 480
```

```
Lys Lys Arg Tyr Asp Leu Ser Ala Leu Val Arg His Ala Glu Pro Glu
                485                 490                 495
Gln Asn Trp Glu Ala Val Asp Gly Ser Gln Thr Glu Thr Glu Lys Lys
            500                 505                 510
His Phe Phe Ile Asn Ile Cys His Arg Val Leu Gln Glu Gly Lys Ala
            515                 520                 525
Arg Gly Cys Pro Glu Asp Ala Ala Val Cys Ala Val Asp Lys Asn Gly
530                 535                 540
Ser Lys Asn Leu Gly Lys Phe Ile Ser Ser Pro Met Lys Glu Lys Gly
545                 550                 555                 560
Asn Ile Gln Leu Ser Tyr Ser Asp Gly Asp Cys Gly His Gly Lys
                565                 570                 575
Lys Ile Lys Thr Asn Ile Thr Leu Val Cys Lys Pro Gly Asp Leu Glu
            580                 585                 590
Ser Ala Pro Val Leu Arg Thr Ser Gly Glu Gly Gly Cys Phe Tyr Glu
            595                 600                 605
Phe Glu Trp Arg Thr Ala Ala Ala Cys Val Leu Ser Lys Thr Glu Gly
            610                 615                 620
Glu Asn Cys Thr Val Phe Asp Ser Gln Ala Gly Phe Ser Phe Asp Leu
625                 630                 635                 640
Ser Pro Leu Thr Lys Lys Asn Gly Ala Tyr Lys Val Glu Thr Lys Lys
                645                 650                 655
Tyr Asp Phe Tyr Ile Asn Val Cys Gly Pro Val Ser Val Ser Pro Cys
                660                 665                 670
Gln Pro Asp Ser Gly Ala Cys Gln Val Ala Lys Ser Asp Glu Lys Thr
            675                 680                 685
Trp Asn Leu Gly Leu Ser Asn Ala Lys Leu Ser Tyr Tyr Asp Gly Met
            690                 695                 700
Ile Gln Leu Asn Tyr Arg Gly Gly Thr Pro Tyr Asn Asn Glu Arg His
705                 710                 715                 720
Thr Pro Arg Ala Thr Leu Ile Thr Phe Leu Cys Asp Arg Asp Ala Gly
                725                 730                 735
Val Gly Phe Pro Glu Tyr Gln Glu Glu Asp Asn Ser Thr Tyr Asn Phe
                740                 745                 750
Arg Trp Tyr Thr Ser Tyr Ala Cys Pro Glu Glu Pro Leu Glu Cys Val
            755                 760                 765
Val Thr Asp Pro Ser Thr Leu Glu Gln Tyr Asp Leu Ser Ser Leu Ala
770                 775                 780
Lys Ser Glu Gly Gly Leu Gly Gly Asn Trp Tyr Ala Met Asp Asn Ser
785                 790                 795                 800
Gly Glu His Val Thr Trp Arg Lys Tyr Tyr Ile Asn Val Cys Arg Pro
                805                 810                 815
Leu Asn Pro Val Pro Gly Cys Asn Arg Tyr Ala Ser Ala Cys Gln Met
            820                 825                 830
Lys Tyr Glu Lys Asp Gln Gly Ser Phe Thr Glu Val Val Ser Ile Ser
            835                 840                 845
Asn Leu Gly Met Ala Lys Thr Gly Pro Val Val Glu Asp Ser Gly Ser
850                 855                 860
Leu Leu Leu Glu Tyr Val Asn Gly Ser Ala Cys Thr Thr Ser Asp Gly
865                 870                 875                 880
Arg Gln Thr Thr Tyr Thr Thr Arg Ile His Leu Val Cys Ser Arg Gly
                885                 890                 895
Arg Leu Asn Ser His Pro Ile Phe Ser Leu Asn Trp Glu Cys Val Val
```

-continued

```
                900                  905                  910
Ser Phe Leu Trp Asn Thr Glu Ala Ala Cys Pro Ile Gln Thr Thr Thr
            915                  920                  925

Asp Thr Asp Gln Ala Cys Ser Ile Arg Asp Pro Asn Ser Gly Phe Val
    930                  935                  940

Phe Asn Leu Asn Pro Leu Asn Ser Ser Gln Gly Tyr Asn Val Ser Gly
945                  950                  955                  960

Ile Gly Lys Ile Phe Met Phe Asn Val Cys Gly Thr Met Pro Val Cys
                965                  970                  975

Gly Thr Ile Leu Gly Lys Pro Ala Ser Gly Cys Glu Ala Thr Gln
            980                  985                  990

Thr Glu Glu Leu Lys Asn Trp Lys Pro Ala Arg Pro Val Gly Ile Glu
        995                  1000                 1005

Lys Ser Leu Gln Leu Ser Thr Glu Gly Phe Ile Thr Leu Thr Tyr Lys
    1010                 1015                 1020

Gly Pro Leu Ser Ala Lys Gly Thr Ala Asp Ala Phe Ile Val Arg Phe
1025                 1030                 1035                 1040

Val Cys Asn Asp Asp Val Tyr Ser Gly Pro Leu Lys Phe Leu His Gln
            1045                 1050                 1055

Asp Ile Asp Ser Gly Gln Gly Ile Arg Asn Thr Tyr Phe Glu Phe Glu
            1060                 1065                 1070

Thr Ala Leu Ala Cys Val Pro Ser Pro Val Asp Cys Gln Val Thr Asp
            1075                 1080                 1085

Leu Ala Gly Asn Glu Tyr Asp Leu Thr Gly Leu Ser Thr Val Arg Lys
        1090                 1095                 1100

Pro Trp Thr Ala Val Asp Thr Ser Val Asp Gly Arg Lys Arg Thr Phe
1105                 1110                 1115                 1120

Tyr Leu Ser Val Cys Asn Pro Leu Pro Tyr Ile Pro Gly Cys Gln Gly
                1125                 1130                 1135

Ser Ala Val Gly Ser Cys Leu Val Ser Glu Gly Asn Ser Trp Asn Leu
            1140                 1145                 1150

Gly Val Val Gln Met Ser Pro Gln Ala Ala Ala Asn Gly Ser Leu Ser
            1155                 1160                 1165

Ile Met Tyr Val Asn Gly Asp Lys Cys Gly Asn Gln Arg Phe Ser Thr
    1170                 1175                 1180

Arg Ile Thr Phe Glu Cys Ala Gln Ile Ser Gly Ser Pro Ala Phe Gln
1185                 1190                 1195                 1200

Leu Gln Asp Gly Cys Glu Tyr Val Phe Ile Trp Arg Thr Val Glu Ala
            1205                 1210                 1215

Cys Pro Val Val Arg Val Glu Gly Asp Asn Cys Glu Val Lys Asp Pro
        1220                 1225                 1230

Arg His Gly Asn Leu Tyr Asp Leu Lys Pro Leu Gly Leu Asn Asp Thr
    1235                 1240                 1245

Ile Val Ser Ala Gly Glu Tyr Thr Tyr Tyr Phe Arg Val Cys Gly Lys
        1250                 1255                 1260

Leu Ser Ser Asp Val Cys Pro Thr Ser Asp Lys Ser Lys Val Val Ser
1265                 1270                 1275                 1280

Ser Cys Gln Glu Lys Arg Glu Pro Gln Gly Phe His Lys Val Ala Gly
            1285                 1290                 1295

Leu Leu Thr Gln Lys Leu Thr Tyr Glu Asn Gly Leu Leu Lys Met Asn
        1300                 1305                 1310

Phe Thr Gly Gly Asp Thr Cys His Lys Val Tyr Gln Arg Ser Thr Ala
        1315                 1320                 1325
```

```
Ile Phe Phe Tyr Cys Asp Arg Gly Thr Gln Arg Pro Val Phe Leu Lys
    1330                1335                1340
Glu Thr Ser Asp Cys Ser Tyr Leu Phe Glu Trp Arg Thr Gln Tyr Ala
1345                1350                1355                1360
Cys Pro Pro Phe Asp Leu Thr Glu Cys Ser Phe Lys Asp Gly Ala Gly
                1365                1370                1375
Asn Ser Phe Asp Leu Ser Ser Leu Ser Arg Tyr Ser Asp Asn Trp Glu
            1380                1385                1390
Ala Ile Thr Gly Thr Gly Asp Pro Glu His Tyr Leu Ile Asn Val Cys
        1395                1400                1405
Lys Ser Leu Ala Pro Gln Ala Gly Thr Glu Pro Cys Pro Pro Glu Ala
    1410                1415                1420
Ala Ala Cys Leu Leu Gly Gly Ser Lys Pro Val Asn Leu Gly Arg Val
1425                1430                1435                1440
Arg Asp Gly Pro Gln Trp Arg Asp Gly Ile Ile Val Leu Lys Tyr Val
                1445                1450                1455
Asp Gly Asp Leu Cys Pro Asp Gly Ile Arg Lys Lys Ser Thr Thr Ile
            1460                1465                1470
Arg Phe Thr Cys Ser Glu Ser Gln Val Asn Ser Arg Pro Met Phe Ile
        1475                1480                1485
Ser Ala Val Glu Asp Cys Glu Tyr Thr Phe Ala Trp Pro Thr Ala Thr
    1490                1495                1500
Ala Cys Pro Met Lys Ser Asn Glu His Asp Asp Cys Gln Val Thr Asn
1505                1510                1515                1520
Pro Ser Thr Gly His Leu Phe Asp Leu Ser Ser Leu Ser Gly Arg Ala
                1525                1530                1535
Gly Phe Thr Ala Ala Tyr Ser Glu Lys Gly Leu Val Tyr Met Ser Ile
            1540                1545                1550
Cys Gly Glu Asn Glu Asn Cys Pro Pro Gly Val Gly Ala Cys Phe Gly
        1555                1560                1565
Gln Thr Arg Ile Ser Val Gly Lys Ala Asn Lys Arg Leu Arg Tyr Val
    1570                1575                1580
Asp Gln Val Leu Gln Leu Val Tyr Lys Asp Gly Ser Pro Cys Pro Ser
1585                1590                1595                1600
Lys Ser Gly Leu Ser Tyr Lys Ser Val Ile Ser Phe Val Cys Arg Pro
                1605                1610                1615
Glu Ala Gly Pro Thr Asn Arg Pro Met Leu Ile Ser Leu Asp Lys Gln
            1620                1625                1630
Thr Cys Thr Leu Phe Phe Ser Trp His Thr Pro Leu Ala Cys Glu Gln
        1635                1640                1645
Ala Thr Glu Cys Ser Val Arg Asn Gly Ser Ser Ile Val Asp Leu Ser
    1650                1655                1660
Pro Leu Ile His Arg Thr Gly Gly Tyr Glu Ala Tyr Asp Glu Ser Glu
1665                1670                1675                1680
Asp Asp Ala Ser Asp Thr Asn Pro Asp Phe Tyr Ile Asn Ile Cys Gln
                1685                1690                1695
Pro Leu Asn Pro Met His Ala Val Pro Cys Pro Ala Gly Ala Ala Val
            1700                1705                1710
Cys Lys Val Pro Ile Asp Gly Pro Pro Ile Asp Ile Gly Arg Val Ala
        1715                1720                1725
Gly Pro Pro Ile Leu Asn Pro Ile Ala Asn Glu Ile Tyr Leu Asn Phe
    1730                1735                1740
```

-continued

```
Glu Ser Ser Thr Pro Cys Leu Ala Asp Lys His Phe Asn Tyr Thr Ser
1745                1750                1755                1760

Leu Ile Ala Phe His Cys Lys Arg Gly Val Ser Met Gly Thr Pro Lys
            1765                1770                1775

Leu Leu Arg Thr Ser Glu Cys Asp Phe Val Phe Glu Trp Glu Thr Pro
            1780                1785                1790

Val Val Cys Pro Asp Glu Val Arg Met Asp Gly Cys Thr Leu Thr Asp
        1795                1800                1805

Glu Gln Leu Leu Tyr Ser Phe Asn Leu Ser Ser Leu Ser Thr Ser Thr
    1810                1815                1820

Phe Lys Val Thr Arg Asp Ser Arg Thr Tyr Ser Val Gly Val Cys Thr
1825                1830                1835                1840

Phe Ala Val Gly Pro Glu Gln Gly Gly Cys Lys Asp Gly Val Cys
            1845                1850                1855

Leu Leu Ser Gly Thr Lys Gly Ala Ser Phe Gly Arg Leu Gln Ser Met
            1860                1865                1870

Lys Leu Asp Tyr Arg His Gln Asp Glu Ala Val Val Leu Ser Tyr Val
        1875                1880                1885

Asn Gly Asp Arg Cys Pro Pro Glu Thr Asp Asp Gly Val Pro Cys Val
    1890                1895                1900

Phe Pro Phe Ile Phe Asn Gly Lys Ser Tyr Glu Glu Cys Ile Ile Glu
1905                1910                1915                1920

Ser Arg Ala Lys Leu Trp Cys Ser Thr Thr Ala Asp Tyr Asp Arg Asp
            1925                1930                1935

His Glu Trp Gly Phe Cys Arg His Ser Asn Ser Tyr Arg Thr Ser Ser
            1940                1945                1950

Ile Ile Phe Lys Cys Asp Glu Asp Glu Asp Ile Gly Arg Pro Gln Val
        1955                1960                1965

Phe Ser Glu Val Arg Gly Cys Asp Val Thr Phe Glu Trp Lys Thr Lys
    1970                1975                1980

Val Val Cys Pro Pro Lys Lys Leu Glu Cys Lys Phe Val Gln Lys His
1985                1990                1995                2000

Lys Thr Tyr Asp Leu Arg Leu Leu Ser Ser Leu Thr Gly Ser Trp Ser
            2005                2010                2015

Leu Val His Asn Gly Val Ser Tyr Tyr Ile Asn Leu Cys Gln Lys Ile
            2020                2025                2030

Tyr Lys Gly Pro Leu Gly Cys Ser Glu Arg Ala Ser Ile Cys Arg Arg
        2035                2040                2045

Thr Thr Thr Gly Asp Val Gln Val Leu Gly Leu Val His Thr Gln Lys
    2050                2055                2060

Leu Gly Val Ile Gly Asp Lys Val Val Thr Tyr Ser Lys Gly Tyr
2065                2070                2075                2080

Pro Cys Gly Gly Asn Lys Thr Ala Ser Ser Val Ile Glu Leu Thr Cys
            2085                2090                2095

Thr Lys Thr Val Gly Arg Pro Ala Phe Lys Arg Phe Asp Ile Asp Ser
            2100                2105                2110

Cys Thr Tyr Tyr Phe Ser Trp Asp Ser Arg Ala Ala Cys Ala Val Lys
        2115                2120                2125

Pro Gln Glu Val Gln Met Val Asn Gly Thr Ile Thr Asn Pro Ile Asn
    2130                2135                2140

Gly Lys Ser Phe Ser Leu Gly Asp Ile Tyr Phe Lys Leu Phe Arg Ala
2145                2150                2155                2160

Ser Gly Asp Met Arg Thr Asn Gly Asp Asn Tyr Leu Tyr Glu Ile Gln
```

-continued

```
                    2165                    2170                    2175
Leu Ser Ser Ile Thr Ser Ser Arg Asn Pro Ala Cys Ser Gly Ala Asn
                2180                2185                2190
Ile Cys Gln Val Lys Pro Asn Asp Gln His Phe Ser Arg Lys Val Gly
            2195                2200                2205
Thr Ser Asp Lys Thr Lys Tyr Tyr Leu Gln Asp Gly Asp Leu Asp Val
        2210                2215                2220
Val Phe Ala Ser Ser Ser Lys Cys Gly Lys Asp Lys Thr Lys Ser Val
2225                2230                2235                2240
Ser Ser Thr Ile Phe Phe His Cys Asp Pro Leu Val Glu Asp Gly Ile
                2245                2250                2255
Pro Glu Phe Ser His Glu Thr Ala Asp Cys Gln Tyr Leu Phe Ser Trp
            2260                2265                2270
Tyr Thr Ser Ala Val Cys Pro Leu Gly Val Gly Phe Asp Ser Glu Asn
        2275                2280                2285
Pro Gly Asp Asp Gly Gln Met His Lys Gly Leu Ser Glu Arg Ser Gln
    2290                2295                2300
Ala Val Gly Ala Val Leu Ser Leu Leu Leu Val Ala Leu Thr Cys Cys
2305                2310                2315                2320
Leu Leu Ala Leu Leu Leu Tyr Lys Lys Glu Arg Arg Glu Thr Val Ile
                2325                2330                2335
Ser Lys Leu Thr Thr Cys Cys Arg Arg Ser Ser Asn Val Ser Tyr Lys
            2340                2345                2350
Tyr Ser Lys Val Asn Lys Glu Glu Glu Thr Asp Glu Asn Glu Thr Glu
        2355                2360                2365
Trp Leu Met Glu Glu Ile Gln Leu Pro Pro Arg Gln Gly Lys Glu
    2370                2375                2380
Gly Gln Glu Asn Gly His Ile Thr Thr Lys Ser Val Lys Ala Leu Ser
2385                2390                2395                2400
Ser Leu His Gly Asp Asp Gln Asp Ser Glu Asp Glu Val Leu Thr Ile
                2405                2410                2415
Pro Glu Val Lys Val His Ser Gly Arg Gly Ala Gly Ala Glu Ser Ser
            2420                2425                2430
His Pro Val Arg Asn Ala Gln Ser Asn Ala Leu Gln Glu Arg Glu Asp
        2435                2440                2445
Asp Arg Val Gly Leu Val Arg Gly Glu Lys Ala Arg Lys Gly Lys Ser
    2450                2455                2460
Ser Ser Ala Gln Gln Lys Thr Val Ser Ser Thr Lys Leu Val Ser Phe
2465                2470                2475                2480
His Asp Asp Ser Asp Glu Asp Leu Leu His Ile
                2485                2490
```

BINDING OF RETINOIDS TO M6P/IGF-II RECEPTOR

Statement as to Federally Sponsored Research

Work on this invention was support by National Institutes of Health Grant DK-38165. Therefore, the federal government may have rights in the invention.

BACKGROUND OF THE INVENTION

Retinoic acid (RA) and its analogs (retinoids) exert diverse biological effects on normal growth, fetal development, cell differentiation, morphogenesis, metabolism and homeostasis (Deluca, 1991, *FASEB J.* 5:2924–2933; Sporn et al., 1994, *The Retinoids: Biology, Chemistry* and *Medicine*, 2nd Ed., Raven Press, New York). Retinoids have been linked to the induction of apoptosis (Ahuja et al., 1997, *Dev. Biol.* 208:466–481). Effects of retinoids have been shown to be mediated through two classes of nuclear receptors, i.e., the retinoic acid receptors (RARs) and the retinoid X receptors, which are members of the steroid/thyroid hormone receptor superfamily (Pfahl, 1994, *Semin. Cell. Biol.* 5:95–103; Mangelsdorf et al., 1995, *Cell* 83:841–850; Chambon, 1996, *FASEB J.* 10:940–954).

The mannose 6-phosphate/insulin-like growth factor II receptor (M6P/IGF2R protein) is a multifunctional transmembrane glycoprotein that consists of a 300 kDa single polypeptide chain with a large extracellular domain containing 15 repeat regions and a small cytoplasmic domain (Kornfeld, 1992, *Ann. Rev. Biochem.* 61:307–330). The expression of this receptor is developmentally regulated, with the receptor being high in fetal and neonatal tissues (including plasma and heart) and declining postnatally (Nissley et al., 1993, *Mol. Reprod. Dev.* 35:408–413). This receptor binds both mannose 6-phosphate (M6P) and insulin-like growth factor II (IGF-II) at separate sites (MacDonal et al., 1988, *Science* 239:1134–1137; Morgan et al., 1987, *Nature* 329:301–307; Kiess et al., 1988, *J. Biol. Chem.* 263:9339–9344). One function of the receptor is to bind and transport M6P-bearing glycoproteins (e.g. lysosomal enzymes) from the trans-Golgi network or the cell surface to lysosomes (Kornfeld, supra). The cell surface M6P/IGF-II receptor also binds and internalizes IGF-II, resulting in the lysosomal degradation of this ligand (Oka et al., *J.Biol. Chem.* 260:9435–9442). Thus, the receptor suppresses IGF-II proliferative effects. In addition, the M6P/IGF2R protein binds the latent transforming growth factor-β (LTGF-β), permitting cleavage into its active form (TGF-β), a potent growth inhibitor for most cell types (Dennis, et al., 1991, *Proc. Natl. Acad. Sci. USA* 88:580–584). Thus, the M6P/IGF-II receptor plays a role in the regulation of cell growth, and it has anti-cancer activity (Hankins et al., *Oncogene* 12:2003–2009; Sousa et al., 1995, *Nature Genetics* 11:447–449; Wang et al., 1997, *Cancer Res.* 57:2543–2546).

SUMMARY OF THE INVENTION

We have unexpectedly discovered that RA binds to the M6P/IGF2R protein with high affinity and thereby enhances the biological functions of the receptor. Those functions include the binding of M6P-ligands, the trafficking of lysosomal enzymes from the TGN to the lysosomes, and internalization (endocytosis) of exogenous M6P-containing glycoproteins and IGF-II. The interaction of RA with the M6P/IGF2R protein inhibits cell proliferation or induces apoptosis, or both.

Based on these discoveries, the invention provides a method for inhibiting proliferation of a cell or inducing apoptosis. In general, the method includes the steps of providing an elevated level of M6P/IGF2R protein in the cell; and contacting the cell with a compound that binds to the M6P/IGF2R protein. The elevated level of M6P/IGF2R protein in the cell can be achieved by providing a nucleic acid vector containing a M6P/IGF2R-encoding nucleotide sequence operably linked to an expression control sequence, and introducing the vector into the cell, where the M6P/IGF2R-encoding nucleotide sequence expresses M6P/IGF2R protein. The method can be used to inhibit proliferation of a cancer cell or induce apoptosis in a cancer cell. The cancer cell can be in vivo, e.g., in a human or a nonhuman mammal.

In preferred embodiments of the invention, the compound that binds to the M6P/IGF2R protein is a retinoid, but the compound is not required to be a retinoid. Examples of retinoids useful in the invention include retinoic acid, 13-cis-retinoic acid, 9-cis-retinoic acid, retinol, and retinol acetate.

The invention also provides another method for inhibiting proliferation of a cell or inducing apoptosis. This method includes contacting the cell with a retinoid that binds to an M6P/IGF2R protein and does not substantially affect a nuclear retinoic acid receptor-mediated process. Optionally, this method includes providing an elevated level of M6P/IGF2R protein in the cell (as described above).

The invention also provides a method for potentiating an MGP/IGF2R-mediated effect in a cell. The method includes contacting the cell with a first compound that binds directly to a first binding site on an M6P/IGF2R protein, and contacting the cell with a second compound that binds to a second binding site on an M6P/IGF2R protein. The first compound can be mannose-6-phosphate or an insulin-like growth factor. In some embodiments, the second compound does not substantially affect a nuclear retinoic acid receptor-mediated process. Preferably, the second compound is a retinoid, e.g., retinoic acid, 13-cis-retindic acid, 9-cis-retinoic acid, retinol, or retinol acetate. In preferred embodiments, the second binding site is located in repeat 15 of the M6P/IGF2R protein, and it includes amino acids 2213 to 2258 of the M6P/IGF2R protein. The method can be used in a cancer cell. The cancer cell can be in vivo, e.g., in a human or a nonhuman mammal. Typically, the M6P/IGF2R-mediated effect is inhibition of cell proliferation or induction of apoptosis.

The invention also provides an in vitro screening method for identification of compounds that bind directly to the retinoic acid binding site of a M6P/IGF2R protein. The method includes providing M6P/IGFR2 protein substantially free of nuclear retinoic acid receptor proteins; contacting the M6P/IGFR2 protein with a candidate compound; and detecting binding of the candidate compound to the M6P/IGFR2 protein. Preferably, the M6P/IGFR2 protein is immobilized, for example on an affinity chromatography column. Preferably, the candidate compound is a retinoid. The binding can be detected by a radioactive label. Preferred binding assays involve competitive inhibition.

The invention also provides a cellular screening method for identification of compounds that bind directly to the retinoic acid binding site of a M6P/IGF2R protein. The method includes providing a test cell; contacting the test cell with a candidate compound; and detecting enhancement of an M6P/IGF2R protein-related process in the cell. Examples of M6P/IGF2R protein-related processes are M6P/IGF2R protein trafficking in the cell, and an increase in an M6P/IGF2R protein-mediated function. Examples of M6P/IGF2R protein-mediated functions are binding of M6P/IGF2R protein to mannose-6-phosphate, and endocytosis of lysosomal proteins.

As used herein, "retinoic acid" or "RA" means all-trans-retinoic acid, unless otherwise indicated.

As used herein, "retinoid" includes retinoic acid, unless otherwise indicated.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the present invention, the preferred methods and materials are described below. The materials, methods, and examples are illustrative only and not intended to be limiting. Other features and advantages of the invention will be apparent from the detailed description, and from the claims.

BRIEF DESCRIPTION OF THE DRAWINGS

FIG. 7A shows the intracellular localization of the M6P/IGF2R in non-treated fibroblasts by immunofluorescence using anti-M6P/IGF2R antibodies. The receptor was concentrated primarily in the perinuclear structure (probably the TGN area). FIG. 7B shows distribution of the M6P/IGF2R in RA-treated cells. After treatment with RA (1 μM for 3 h), the receptor translocated from perinuclear area to cytoplasmic vesicles (possibly the endosomes and lysosomes) throughout the cytoplasm of the cells. Bar represents 4 μm.

FIG. 8A shows intracellular localization of cathepsin B in non-treated fibroblasts by immunofluorescence using anti-cathepsin B antibodies. The enzyme was found mainly in the perinuclear area. FIG. 8B shows distribution of cathepsin B in RA-treated Cells. After treatment with RA (1 μM for 3 h), the enzyme translocated from the perinuclear area to the cytoplasmic vesicles. Bar represents 4 μm.

DETAILED DESCRIPTION OF THE INVENTION

Figure 1:
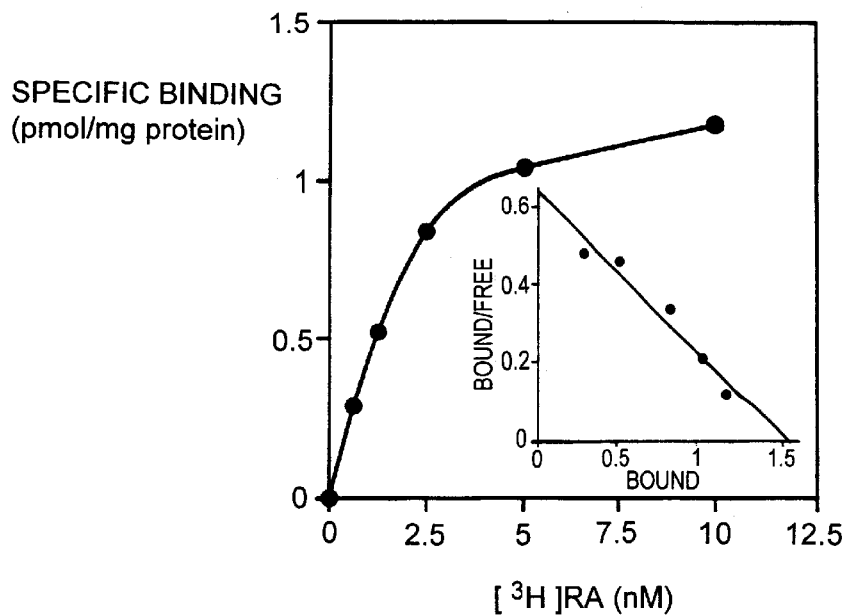
FIG. 1 is a Scatchard plot showing that retinoic acid binds to the M6P/IGF2R protein with high affinity. Partially Purified M6P/IGF-II receptor from neonatal rat serum was incubated with increasing concentrations of [$^3$H]RA in the absence (total binding) or presence (nonspecific binding) of 200-fold excess unlabeled RA. Nonspecific binding was subtracted from total binding and plotted as specific binding. Specific RA binding to M6P/IGF2R was transformed by Scatchard analysis and plotted. Linear regression yielded a $K_D$=2.4 nM (r=0.97).

Enhancing, i.e., triggering, increasing, or potentiating, M6P/IGF2R-mediated effects according to the invention is useful for inhibiting cell proliferation or inducing apoptosis, or both. In turn, inhibiting cell proliferation or inducing apoptosis is useful for treating or preventing cancer. Screening methods for identifying compounds that bind directly to the RA binding site on M6P/IGF2R can be used to discover additional compounds, e.g., new retinoids, for enhancing M6P/IGF2R-mediated effects. Compounds identified in screening methods may have higher affinity for the RA binding site on M6P/IGF2R, or may otherwise exert a stronger effect on the M6P/IGF2R protein, thus enhancing receptor function.

A cell's rate of proliferation (division) can be determined readily by one of ordinary skill in the art. For example, a cell's rate of division can be measured by counting the difference in cell number at two time points, taking the $\log_2$ of that difference, and dividing that value by the time elapsed between the two time points.

Retinoids

In some embodiments of the invention, a retinoid binds to the RA binding site of an M6P/IGF2R protein. The chemical structure of RA (all-trans-retinoic acid is shown below.

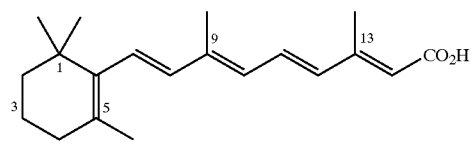

Numerous analogs and derivatives of RA, i.e., retinoids, are known in the art and can be used in the invention. The chemical structures of a wide variety of retinoids can be found in numerous references, e.g., U.S. Pat. No. 5,576,349;

Shi-Yong, et al., 1997, *Cancer Res.* 57:4931–4939; Sporn et al., supra; Apfel et al., 1991, "Synthetic Retinoids: Differential Binding to Retinoic Acid Receptors," in Retinoids: 10 Years On (Saurat, ed.), Basel, Kargen, pp. 110–120. Various retinoids are available commercially. Numerous additional retinoids can be synthesized according to known methods.

Elevating M6P/IGF2R Level

Nucleic acids encoding M6P/IGF2R proteins are useful in, the methods of the invention. Such nucleic acids are readily obtained by one of ordinary skill in the art without undue experimentation. For example, the human M6P/IGF2R amino acid sequence (SEQ ID NO:1) and the transcript sequence encoding it are described in Oshima et al., 1988, *J. Biol. Chem.* 263:2553–2562; Lobel et al., 1988, *J. Biol. Chem.* 263:2563–2570. The sequences were also submitted to GenBank and are available as Accession No. Y00285. From this available sequence information, the skilled person can obtain a nucleic acid encoding the human M6P/IGF2R amino acid sequence by amplification from human cDNA by using primers upstream and downstream of the coding sequence, according to conventional PCR techniques.

An elevated level of M6P/IGF2R protein can be provided in a cell by expressing in the cell a nucleic acid construct containing expression control sequences operably linked to a nucleotide sequence encoding the M6P/IGF2R protein. The nucleic acid construct can be derived from a non-replicating linear or circular DNA or RNA vector, or from an autonomously replicating plasmid or viral vector. Alternatively, the construct can be integrated into the target cell's genome. Any vector that can transfect the target cell can be used in the invention. Methods for constructing expression vectors are known in the art (see, e.g., *Molecular Cloning: A Laboratory Manual*, Sambrook et al., eds., Cold Spring Harbor Laboratory, 2nd Edition, Cold Spring Harbor, N.Y. 1989).

In these vectors, a promoter is operably linked to the nucleic acid sequence encoding the M6P/IGF2R protein. Any promoter that directs a high level of transcription in the target cells can be used in the invention. Non-tissue specific promoters, such as the cytomegalovirus (DeBernardi et al., 1991, *Proc. Natl. Acad. Sci. USA* 88:9257–9261, and references therein), mouse metallothionine I gene (Hammer et al., 1982, *J. Mol. Appl. Gen.* 1:273–288), HSV thymidine kinase (McKnight, 1982, *Cell* 31:355–365), and SV40 early (Benoist et al., 1981, *Nature* 290:304–310) promoters are examples of promoters useful in the methods of the invention. The above-described nucleic acid constructs and vectors can be introduced into target cells by any standard method. Exemplary methods are introduction of naked DNA, liposome fusion, biolistic transfer, electroporation, erythrocyte ghosts, or microsphere methods. Microsphere methods include the use of microparticles, which are described in U.S. Pat. No. 4,789,734; U.S. Pat. No. 4,925,673; U.S. Pat. No. 3,625,214; Gregoriadis, *Drug Carriers in Biology and Medicine*, pp. 287–341, Academic Press, 1979.

Alternatively, one can employ a viral-based vector as a means for introducing the nucleic acid into the target cells. The use of a viral-based vector may be preferred, particularly when the target cells are in vivo, e.g., in a human patient. Preferred viral vectors include those derived from replication-defective hepatitis viruses (e.g., HBV and HCV), retroviruses (see, e.g., PCT publication W089/07136; Rosenberg et al., 1990, *New Eng J Med* 323:570–578), adenovirus (see, e.g., Morsey et al., 1993, *J. Cell. Biochem.*, Supp. 17E), adeno-associated virus (Kotin et al., 1990, *Proc. Natl. Acad. Sci. USA* 87:2211–2215), replication defective herpes simplex viruses (HSV; Lu et al., Abstract, page 66, Abstracts of the Meeting on Gene Therapy, Sept. 22–26, 1992, Cold Spring Harbor Laboratory, Cold Spring Harbor, N.Y.), canary pox virus, and any modified versions of these vectors. Viral vectors useful for introducing polypeptides into neuronal cells include adenovirus as described Yoon et al., 1996, *Proc. Natl. Acad. Sci. USA* 93:11974–11979, and Sindbis virus as described in Altman-Hamamdzic et al., 1997, *Gene Therapy* 4:815–822.

Formulations

In some embodiments of the invention, a cell is contacted with a compound that binds to an M6P/IGF2R protein, e.g., RA or a retinoid. When the cell is in vivo, e.g., in a human patient or nonhuman mammal, the compound that binds to the M6P/IGF2R protein can be administered topically, orally, or parenterally. Preferably, the compound is formulated in a pharmaceutical composition.

Liquid dosage forms for oral administration include pharmaceutically acceptable emulsions, microemulsions, solutions, suspensions, syrups and elixirs. In addition to the active compound, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable depot forms are made by forming microencapusule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly (anhydrides) Depot injectable formulations are also prepared by entrapping the drug in liposomes or microemulsions which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, 3) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as, talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Experimental Examples
Photoaffinity Labeling of Proteins with Retinoic Acid

Incubation of the membrane preparations of neonatal rat cardiac myocytes with tritiated RA ([$^3$H]RA), followed by photolysis led to the labeling of a doublet protein at 300 kDa. The protein was not labeled when the sample plus [$^3$H]RA was not irradiated and when the [$^3$H]RA was first photolyzed before mixing with the proteins. Denaturation of the proteins by boiling the membrane sample resulted in loss of the labeling. Incubation with a 50-fold molar excess of nonradioactive all-trans-retinoic acid before photolysis abolished the labeling of the 300 kDa protein. In contrast, other hydrophobic compounds, such as eicosapentaenoic acid (C20:5n-3, EPA), having a molecular weight and structure similar to that of RA, did not cross-link to the 300 kDa protein or competitively inhibit [$^3$H]RA cross-linking to the protein. These results indicated that the [$^3$H]RA cross-linking to the 300 kDa protein was specific.

Identification of Labeled RA-Binding Protein

Because of the molecular weight of the [$^3$H]RA-labeled protein and its abundance in fetal and neonatal tissues, it was suspected that the protein was the mannose-6-phosphate/insulin-like growth factor II receptor (M6P/IGF2R). To verify this, the proteins of neonatal rat serum were immunoprecipitated before or after [$^3$H]RA photolabeling (irradiation) with a polyclonal antibody to rat M6P/IGF-II receptor. The 300 kDa labeled doublet band almost completely disappeared in the sample immunodepleted of the M6P/IGF2R. A single 300 kDa strongly-labeled doublet band appeared in the sample immunoprecipitated by the anti-M6P/IGF-II receptor antibody. The 66 kDa albumin, known to bind RA (Goodman, 1984, *N. England J. Med.* 310:1023–1031), could also be photolabeled by [$^3$H]RA, but its labeling was not significantly affected by the immunoprecipitation with anti-M6P/IGF2R antibody. When excessive molar (50 µM) unlabeled RA was added to the immunoprecipitated protein together with [$^3$H]RA before irradiation, the radiolabel at the 300 kDa protein was lost. Alternatively, immunoprecipitation of [$^3$H]RA-photolabeled protein mixtures of neonatal rat serum with the polyclonal anti-M6P/IGF2R antibody also yielded a single 300 kDa radiolabeled protein. This protein was not precipitated by non-immune rabbit serum or purified IgG, indicating the immunoprecipitation was not nonspecific.

To investigate further the identity of the 300 kDa labeled protein, M6P/IGF2R protein from neonatal rat serum was purified by pentamannosyl-6-phosphate (PMP)-affinity chromatography and then subjected the preparations to affinity-photolabeling with [$^3$H]RA. The purified 300 kDa doublet protein, (identical to that precipitated by the anti-IGF-II receptor antibody), was intensively photolabeled by [$^3$H]RA. In addition, photolabeling experiments using cultured mouse P388D$_1$ cells, known to lack the M6P/IGF2R receptor (Gabel et al., 1983, *Proc. Natl. Acad. Sci. USA* 80:775–779). The 300-kDa [$^3$H]RA-labeled protein band, which was readily detected in the membrane preparation of neonatal rat cardiac myocytes, was absent in P388D, cells. These data demonstrated that the 300 kDa photolabeled protein is indeed the M6P/IGF-II receptor.

Another protein at 260 kDa from neonatal rat serum was also immunoprecipitated by the anti-M6P/IGF-II receptor antibody (FIG. 2C) and M6P-affinity enriched (FIG. 2D), but was not affinity-photolabeled by [$^3$H]RA. The 260 kDa protein appeared to be a truncated form (probably missing the C-terminal region) of the M6P/IGF-II receptor lacking the RA binding site. To investigate this observation, we immunoprecipitated and immunoblotted the 260 kDa protein with two different antibodies: the polyclonal anti-receptor antibody and an anti-peptide antibody that specifically recognizes a 22-amino acid peptide located 32 residues C-terminal to the transmembrane domain of the M6P/IGF-II receptor (provided by Dr. R. G. MacDonald) (MacDonald et al., 1989,*J. Biol. Chem.* 264:3256–3261). The 260 kDa protein was recognized only by the anti-receptor antibody, but not by the anti-peptide antibody, whereas the 300 kDa protein was recognized by both antibodies. It was observed that the 300 kDa labeled protein in the cellular extracts or conditioned medium (serum-free) of cultured neonatal rat cardiac myocytes was specifically recognized by these two antibodies and also exhibited no change to disulfide bond reduction. These results demonstrated that both intact (300 kDa) and truncated (260 kDa) forms of M6P/IGF-II receptor exist in the serum. Since only the intact form (300 kDa) bound RA, it appeared that the 40 kDa C-terminal region, missing from the 300 kDa receptor and containing the cytoplasmic domain needed for rapid endocytosis and efficient lysosomal enzyme sorting, is necessary for RA binding.

Binding Affinity of RA and Other Retinoids

Figure 4:
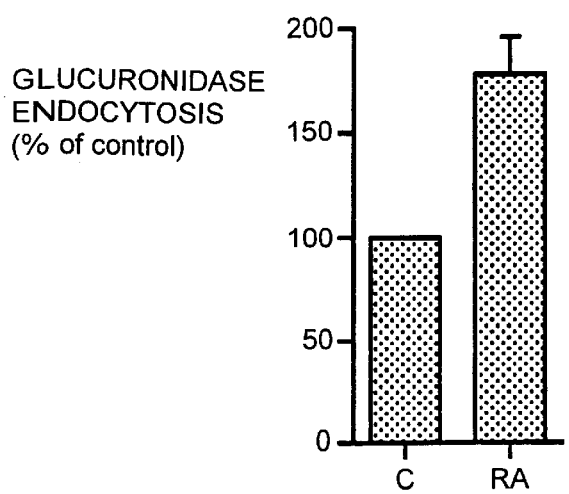
FIG. 4 is a histogram summarizing data on the effect of RA on the endocytosis of exogenous β-glucuronidase. Myocytes were incubated for 2 h at 37°0 C. with 1 ml of MEM containing 10,000 units of human β-glucuronidase, and with or without 5 mM mannose 6-phosphate, in the presence or absence of 2 μM RA. Following the incubation, the internalized human β-glucuronidase was determined as described in the Methods.

To determine the affinity of the binding of [$^3$H]RA to M6P/IGF-II receptor, we performed equilibrium binding of [$^3$H]RA to partially purified rat M6P/IGF-II receptor proteins using the dextran-charcoal absorption technique (27). Scatchard analysis of the binding data revealed a single class of high-affinity binding sites for RA with a $K_D$ of 2.5±0.3 nM (n=3) (FIG. 4).

To demonstrate the role of M6P/IGF2R in mediating RA-induced effects on cell growth, several cell types have been tested for their response to various retinoids. The effects of various RA analogs on the binding of retinoic acid to M6P/IGF2R was examined. Twenty-five to 50-fold molar excess of nonradioactive RA or an RA analog, including 13-cis-RA, 9-cis-RA, retinol and retinol acetate, together with [$^3$H)]RA were incubated with protein samples prior to photolysis, and their effects on the [$^3$H]RA binding were determined. All the retinoids tested inhibited the binding of [$^3$H]RA to M6P/IGF2R. Competitive radioligand (10 nM [$^3$H]RA) binding assay using partially-purified neonatal rat serum IGF2R indicated that the values of IC$_{50}$ (50% inhibitory concentration) for RA, retinol and retinol acetate are 80±26, 120±18, and 135±30 (n=3), respectively. This indicated that retinol and retinol acetate bind to M6P/IGF2R with affinity similar to that of RA. However, polyunsaturated fatty acids (e.g., eicosapentaneoic acid, 20:5n-3), which have structures similar to that of a retinoid, failed to inhibit binding of [$^3$H]RA to M6P/IGF2R. This indicated that: (1) the specific conjugated polyene structure, but not the carbonyl group, is essential for their binding to M6P/IGF2R; and (2) retinol and retinol acetate may be useful for testing the M6P/IGF2R mediated effects, because they bind to the M6P/IGF2R receptor, but not to the nuclear RA receptors.

Interaction of RA with M6P or IGF-II in Binding to M6P/IGF2R Protein

Figure 2:
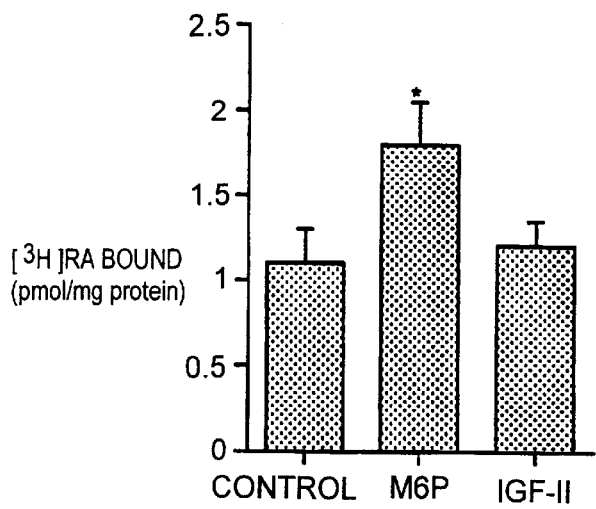
FIG. 2 is a histogram summarizing data on the interaction between RA with M6P (5 mM) and IGF-II (20 μM) on the [$^3$H]RA binding to partially purified M6P/IGF-II receptors. The asterisk indicates p<0.05 (n=4)
Figure 3:
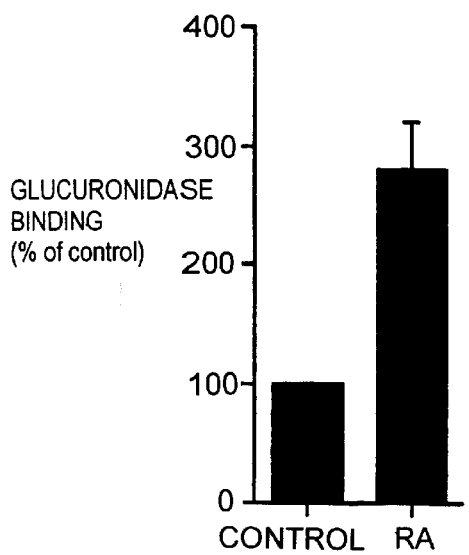
FIG. 3 is a histogram summarizing data on the effect of RA (1 μM) on β-glucuronidase binding to permeabilized neonatal rat cardiac myocytes (n=3).

This was the first demonstration of a single receptor binding three different classes of ligands: M6P (a carbohydrate), IGF-II (a protein) and RA (a lipid). To determine how these ligands interact in binding to the same receptor, we examined the effects of M6P and IGF-II on the [$^3$H]RA-affinity photolabeling of the M6P/IGF-II receptor. Neither M6P nor IGF-II inhibited [$^3$H]RA binding to the M6P/IGF-II receptor. This indicated that they do not bind to the same site. However, M6P, but not IGF-II, significantly enhanced the cross-linking of [$^3$H]RA to M6P/IGF-II receptor. The [$^3$H]RA labeling of M6P/IGF-II receptor was 2-fold greater in the presence of 5 mM M6P than in the absence of M6P, as measured by NIH Image, n=3. Similar results were obtained by measurement of the binding of [$^3$H]RA to the partially purified receptors (FIG. 2). The increased binding of RA to the receptor in the presence of M6P appeared to be the result of increased binding affinity. Dissociation constants for M6P-treated receptor and control were 1.2±0.4 nM and 2.5±0.3 nM, respectively. The lysosomal enzyme, β-glucuronidase (2,500 units/ml), was also shown to increase [$^3$H]RA binding to the receptor. Conversely, examination of the effect of RA on M6P binding to M6P/IGF2R in saponin-permeabilized neonatal rat cardiac myocytes using the M6P-containing lysosomal enzyme, β-glucuronidase, as a probe showed that the M6P-inhibitable binding of the lysosomal enzyme to the cells was 2–3 times higher in the presence of RA (1 μM) than in the absence of RA (FIG. 3). These results indicate a positive cooperativity between M6P and RA binding to M6P/IGF-II-receptor.

RA Effect on M6P/IGF2R Function

Figure 5:
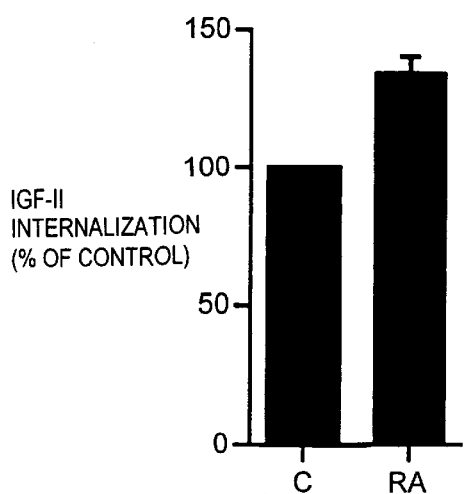
FIG. 5 is a histogram summarizing data on the effect of RA on the internalization of $^{125}$I-IGF-II. Assay was performed by incubating cells at 370° C. for 2 h in media (150 mM NaCl, 5 mM KCl, 1.2 mM MgSO$_4$, 8 mM glucose, 100 mM Hepes, pH 7.6) or F-10 culture medium containing $^{125}$I-IGF-II (0.5 ng/ml) with or without excess unlabeled IGF-II (2 μg/ml), in the presence or absence of 2 μM RA. Following the incubation, the cells were washed three times with ice-cold PBS, and cell-associated radioactivity was determined by a gamma counter.
Figure 6:
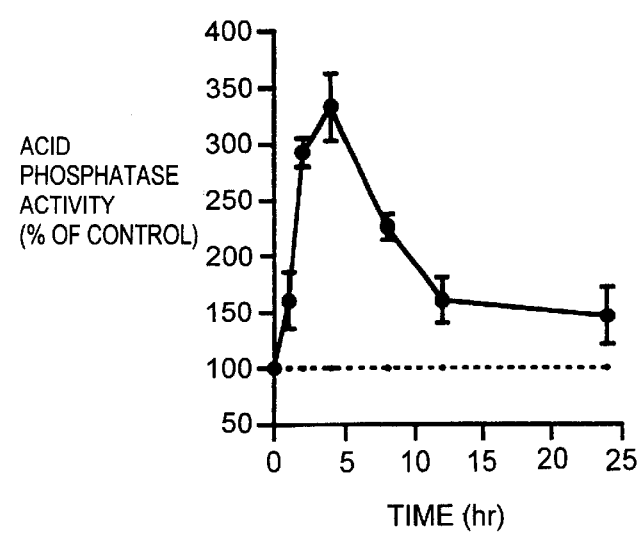
FIG. 6. is a graph summarizing data on the effect of RA on cellular acid phosphatase activity. Cultured neonatal rat cardiac myocytes were treated with 2 μM RA at 37° C. for various time, washed and harvested. Cellular proteins were then solubilized by sonication and acid phosphatase activity was assayed using a Diagnostics Acid Phosphatase kit (Sigma). Dotted line represents control cells. Solid line represents RA-treated cells. Bars represent standard error or the mean (n=4).

The primary functions of the Man-6-P/IGF-II receptor are to mediate endocytosis of extracellular M6P-containing proteins (e.g. lysosomal enzymes) and IGF-II and to sort newly synthesized lysosomal enzymes. Therefore, an important question raised by the direct interaction of RA with M6P/IGF2R is whether RA influences these functions of the receptor. To answer this question, we examined the effect of RA on endocytosis of exogenous β-glucuronidase and $^{125}$I-IGF-II and intracellular activity of acid phosphatase in cultured neonatal rat cardiac myocytes, which were known to express high levels of the M6P/IGF-II receptor (Nissley et al., 1993, *Mol. Reprod. Dev.* 35:408–413). RA at a concentration of 2 μM almost doubled the M6P-inhibitable endocytosis of β-glucuronidase, increased the internalization of IGF-II by 30–50% and induced a transient cellular accumulation of acid phosphatase. This indicated an increased sorting of lysosomal enzymes) (FIGS. 4–6). The structurally-similar lipid, EPA (C20:5n-3), (10 μM) had no such effects. These effects of RA were not altered in the presence of a protein synthesis inhibitor (0.5 mM cycloheximide) and were not observed in the receptor-negative P388D$_1$ cells. This indicated a direct interaction of RA with the M6P/IGF2R protein. These data suggested that RA, upon binding to the M6P/IGF-II receptor, acts as a functional regulator to induce rapid endocytosis and efficient lysosomal enzyme sorting.

Intracellular Trafficking

Figure 7A:
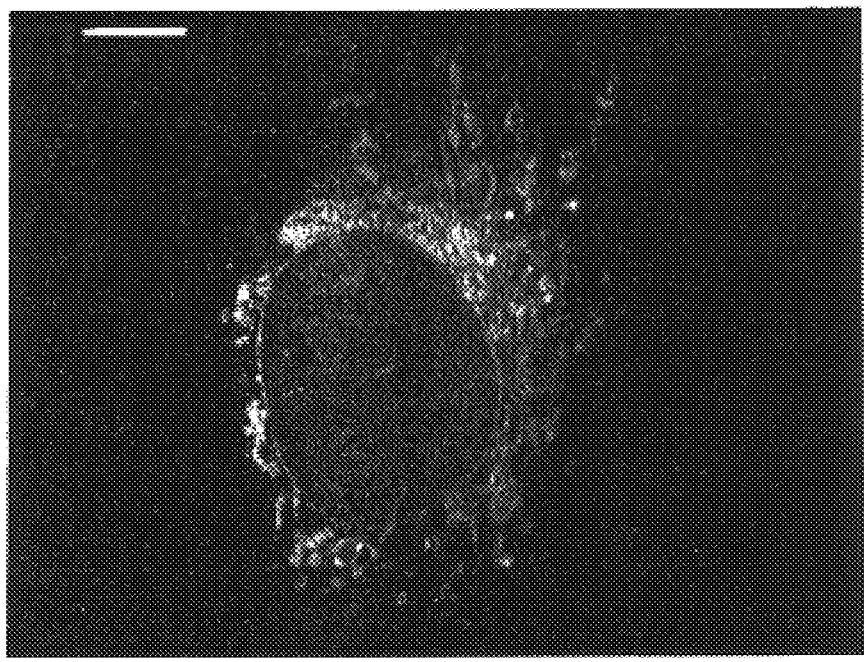
FIGS. 7A and 7B are photo micrographs showing the effect of retinoic acid on the distribution of the M6P/IGF2R in neonatal rat fibroblasts.
Figure 7B:
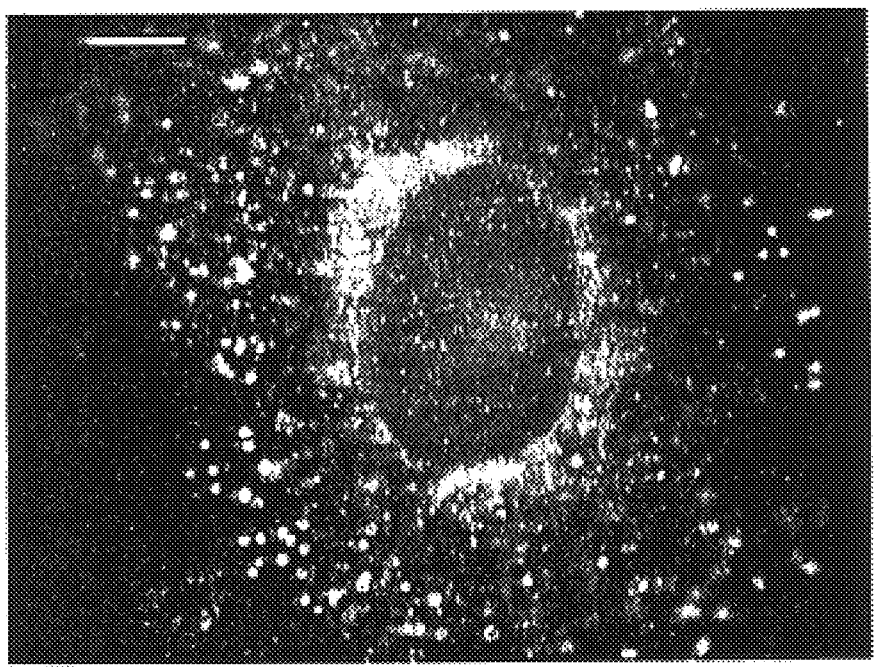
Figure 8A:
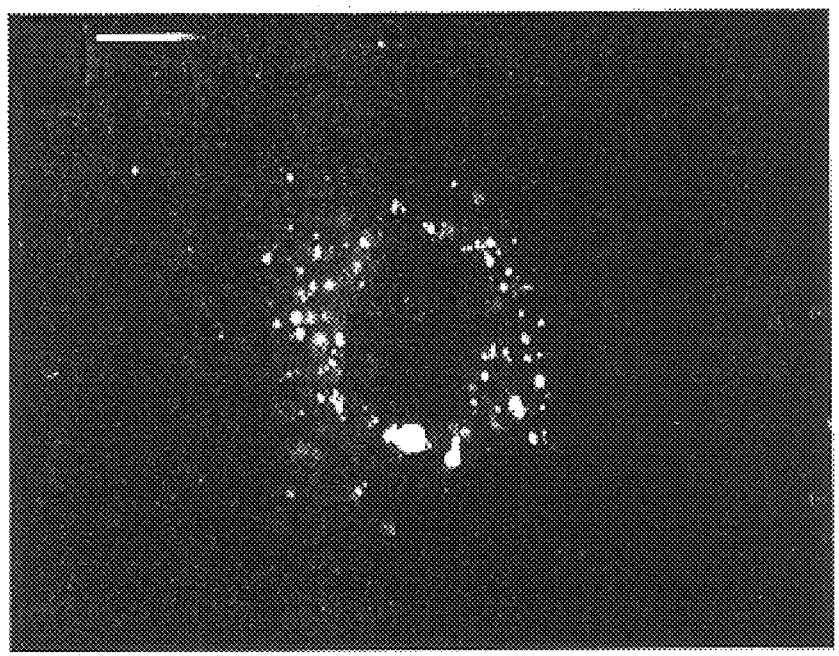
FIGS. 8A and 8B are photomicrographs showing effect of retinoic acid on the distribution of cathepsin B in neonatal rat fibroblasts.
Figure 8B:
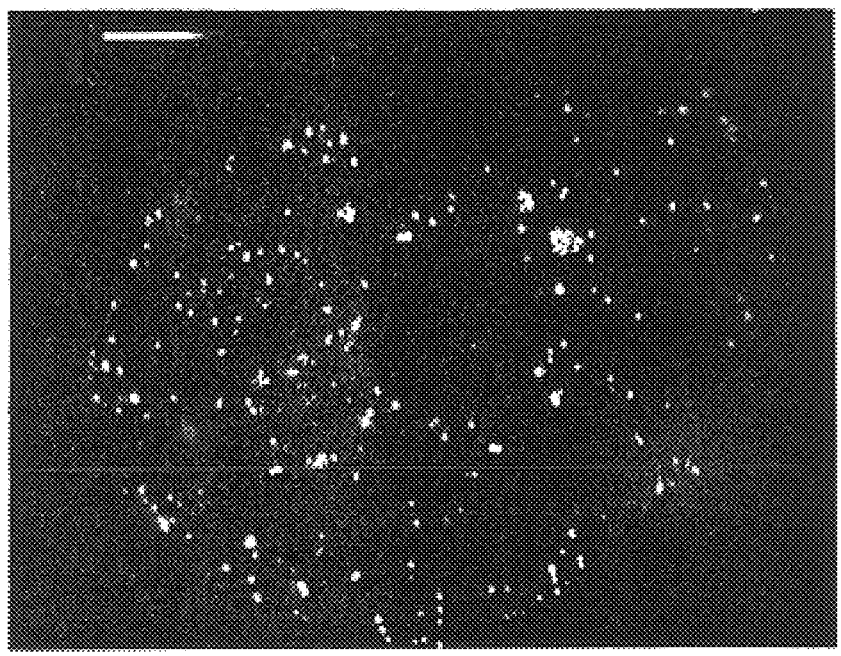

To determine if RA affects intracellular trafficking of the M6P/IGF2R, distribution of the receptor in neonatal rat fibroblasts with or without RA treatment was visualized by immunofluorescence. The primary antibody used to target the receptor was a polyclonal anti-rat M6P/IGF2R (full length) rabbit IgG with high specificity. A non-immuno-rabbit IgG was used as a negative control. As indicated by fluorescence (FIGS. 7A and 7B), the M6P/IGF2R in the fibroblasts is normally concentrated primarily in the perinuclear structure (probably the TGN). When cells were treated with 0.25-1 μM RA for 2–3 h, the profile (distribution) of the receptor in the cells exhibited a dramatic change, characterized by a movement of the receptors from the perinuclear area to the cytoplasmic vesicles (probably the endosomes and lysosomes) throughout the entire cytoplasm of the cell (FIGS. 8A and 8B). This indicated a potentiating effect of RA on the trafficking of the M6P/IGF2R from the TGN to the endosomes/lysosomes.

Since biosynthetic transport of lysosomal enzymes from the TGN to endosomes/lysosomes is mainly mediated by the M6P/IGF2R (Sohar et al., 1998, *Biochem. J.* 330:903–908), an enhanced trafficking of the receptor should lead to an increased translocation of the M6P-containing lysosomal enzymes from the TGN to lysosomes. To test this, we examined the effect of RA on the intracellular distribution of cathepsin B, a lysosomal protease known to be transported in a M6P-dependent manner in fibroblasts (Hanewinkel et al., 1987, *J. Diol. Chem.* 262:12351–12355). Treating the cells with RA resulted in a remarkable change in cathepsin B distribution (FIGS. 8A and 8B). The distribution was similar to that of M6P/IGF2R (shift from perinuclear area to cytoplasmic vesicles throughout the cytoplasm). Thus, it was demonstrated that RA induces intracellular translocation of both M6P/IGF2R and lysosomal enzymes.

Next, we tested whether the effect of RA on the M6P/IGF2R and cathepsin B trafficking could be blocked by a potent RAR antagonist and furthermore, whether the RA effect could be mimicked by a potent RAR agonist. TTNPB, a very potent RAR agonist, and AGN193109, a RAR antagonist able to completely block the action of RA (mediated by RARs) when used at a 10-fold molar excess, were used in these experiments. The effect of RA on the distribution of either M6P/IGF2R or cathepsin B was neither blocked by the RAR antagonist, nor mimicked by the RAR agonist. This indicated that the action of RA in translocation of M6P/IGF2R and cathepsin B was independent of the RARs.

We examined the effect of RA on the distribution of cathepsin B in cells that either lack or over-express the M6P/IGF2R. Mouse macrophage P388D1 cells are the best characterized cells that lack the M6P/IGF2R (Gabel et al., 1983, *Proc. Natl. Acad. Sci. USA* 80:775–779; Kyle et al., 1988, J. Biol. Chem. 263:16230–16235). Transfer of the M6P/IGF2R gene into these cells resulted in a population of P388D1 cells that stably overexpress the receptor (MacDonald et al., supra). The responses of these two different populations of P388D1 cells (with or without MGP/IGF2R), in terms of the RA-induced cathepsin B translocation, were observed. No significant effect of RA was found in the M6P/IGF2R-deficient cells. In contrast, a remarkable cathepsin B translocation, similar to that observed in the fibroblasts, was found in the stably-transfected P388D1 cells overexprssing the M6P/IGF2R. These results indicated that the M6P/IGF2R was mediating the observed effects of RA.

These results demonstrated that RA alters intracellular distribution of the M6P/IGF2R, leading to enhanced trafficking of newly synthesized lysosomal enzymes from the TGN to the endosomes/lysosomes. The RA-induced redistribution of the M6P/IGF2R and the lysosomal enzymes appears to be independent of the action of the RARs.

RA-RecePtor Interaction and Cell Growth

Cultured neonatal rat cardiac myocytes were known to express high levels of the M6P/IGF2R protein. The effect of RA on the growth of normal, neonatal rat cardiac myocytes was examined. Treatment of the cells with µM RA for 48 hours resulted in marked alteration of cell morphology, and inhibition of growth. The RA-treated cells rounded up, lost the spreading attachments, and exhibited much smaller colonies, as compared to controls. Retinol and retinol acetate, have a much lower affinity for nuclear RA receptors than RA, but nevertheless exerted effects on cell morphology and growth similar to the effects of RA. Staining of nuclei with Hoechst 33258 revealed that there were many more apoptotic cells in the RA-treated cultures than in the controls.

Figure 9:
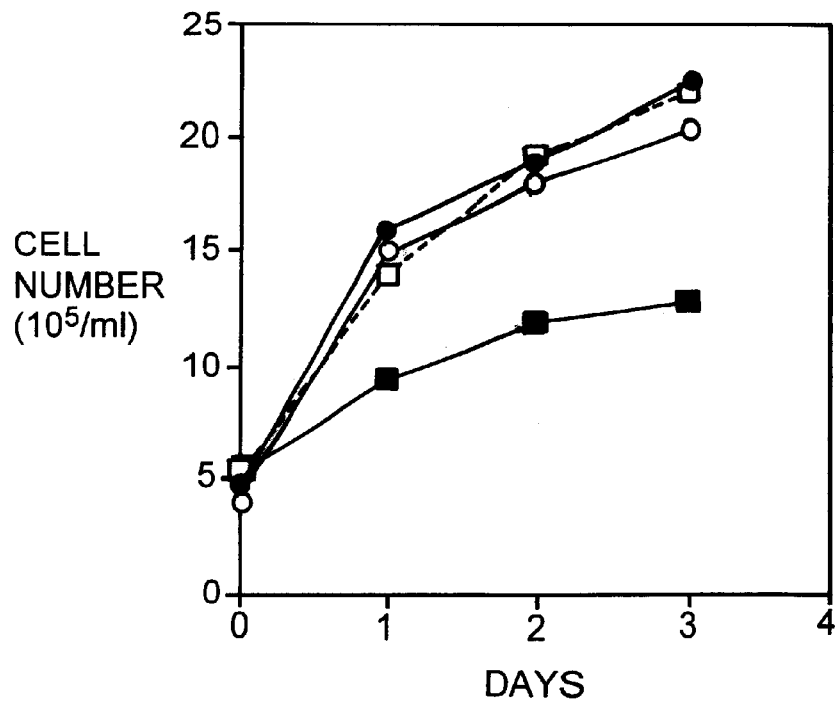
FIG. 9 is a graph showing the effect of RA treatment on growth (number of viable cells) of HL-60R cells overexpressing M6P/IGF2R protein and HL-60R controls. Open circles, vector control cells without RA treatment; closed circles, vector control cells with 1 μM RA treatment; open squares, overexpressing cells without RA treatment; closed squares overexpressing cells with 1 μM RA treatment.

We examined the M6P/IGF2R-mediated effects of RA in the absence of nuclear RA receptors, by using human cell line HL-60R, which lacks functional nuclear RA receptors. This cell line expresses low levels of M6P/IGF2R protein. We transfected HL-60R cells with a plasmid encoding human M6P/IGF2R, so they overexpressed M6P/IGF2R. Then we assessed their response to RA. The cells transfected with the M6P/IGF2R cDNA showed remarkable reduction in growth rate (FIG. 9), and a significant increase in apoptosis, without antecedent differentiation, in response to 1 µM RA. Apoptosis was assayed using FITC-labeled annexin V staining and flow cytometry.

We examined M6P/IGF2R-mediated effects of RA in mouse macrophage P388D1 cells, which are the best characterized cells that lack the M6P/IGF2R protein. They also possess a phenotype that is particularly suited for genetic complementation experiments, i.e., secretion of the majority of lysosomal enzymes and the lack of ability to endocytose exogenous ligands.

Figure 10:
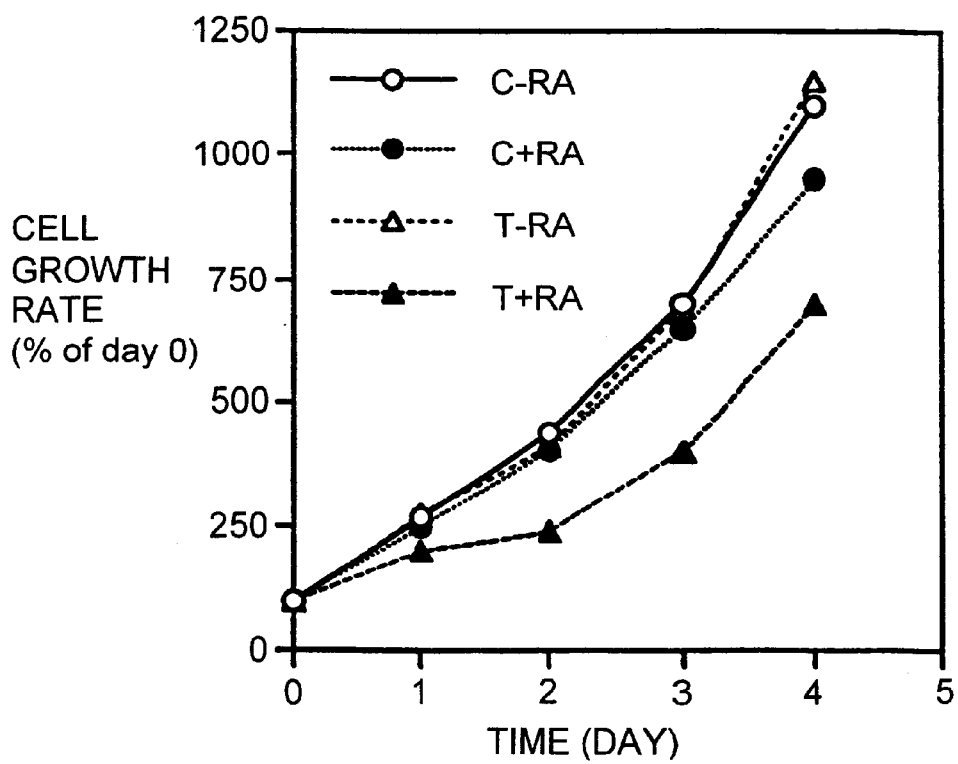
FIG. 10 is a graph showing the effect of RA treatment on growth rate of P388D1 cells overexpressing M6P/IGF2R protein and P388D1 controls. Open circles, vector control cells without RA treatment; closed circles, vector control cells with 1 μM RA treatment; open triangles, overexpressing cells without RA treatment; closed triangles overexpressing cells with 1 μM RA treatment.

Treatment of stably transformed P388D1 cells overexpressing M6P/IGF2R protein with 1 µM RA for 24 hours resulted in remarkable changes in cell morphology, characterized by round shape, smaller size and loss of cell-cell connections or spreading attachments (plasma projections). Control cells (transformed with the vector alone) showed no such changes. Also, the overexpressing cells grew much more slowly in the presence of RA (FIG. 10), indicated an inhibitory effect on cell proliferation. In addition, fluorescence staining of fragmented DNA indicated that a much higher number of apoptotic cells was present in the overexpressing P388D1 cells, as compared to controls. These effects were similarly induced by retinal, retinol, and retinol acetate, but not be eicosapentanoic acid.

Methods and Materials

Cell Isolation and Culture For the photoaffinity labeling experiments, cardiac myocytes were isolated from 1-day-old neonatal Sprague-Dawley rats, using the Neonatal Cardiomyocyte Isolation System (Worthington). The isolated cell were cultured on Petri dishes with culture medium (F-10 nutrient mixture/10% horse serum/5% fetal bovine serum/50 µg/ml streptomycin/50 units/ml penicillin G). Cells were used for experiments after 2–6 days of culture.

Photoaffinity Labeling Photoaffinity labeling was performed essentially according to the methods described in Bernstein et al., 1995, Proc. Natl. Acad. Sci. USA 92:654–658. In darkness or under a red light, 7 µCi of all-trans-[11, 12-$^3$H] retinoic acid (72 Ci/mmol, NEN) with or without 50 µM unlabeled RA (in 10 µl of ethanol) was added to each 1.5 ml microcentrifuge tube. After the ethanol has been evaporated with nitrogen, about 100 µg of proteins of membrane preparations or serum [serum proteins were first concentrated using a Biomax-100K Centrifugal Filter Device (Millipore)] were then added to each tube. The final volume was adjusted to 100 µl with 50 mM Tris buffer (pH 7.4) containing protease inhibitors (5 mM EDTA, 5 mM EGTA, 0.1 mM phenylmethylsulfonyl fluoride, 0.05% NaN$_3$, 20 µg/ml aprotinin, 10 µg/ml benzamidine and 12.5 µg/ml chymostatin) and 50 µM butylated hydroxytoluene (a radical scavenger, used to minimize the non-specific labeling) for a final concentration of 1 µM labeled retinoic acid. The samples were incubated at room temperature with agitation for 1 hour in the dark. The samples were exposed to an intense 365-nm UV light source (Model B 100AP, UPland, CA) for 7 min. Photodestruction of the starting [$^3$H] retinoic acid was completed after 5–6 minute exposure to the UV light, as measured by a spectrophotometer. To remove the non-covalently bound ligands, the photolabeled samples were extracted with chloroform/methanol (2:1), or washed once by centrifugation for membrane samples only).

Fluorography The resultant protein pellets were dissolved in SDS sample buffer containing 5% β-mercapto-ethanol and heated at 100° C. for 5 min. These samples were then run on 7% polyacrylamide gels (30:0.2, acrylamide/bisacrylamide ratio), using conventional SDS/PAGE techniques. After electrophoresis, the gels were stained with Coomassie blue, soaked in Amplifier (Amersham, Life Science) for 30 minutes, dried by a vacuum gel dryer and then exposed to Hyperfilm-TM X-ray films (Amersham, Life Science) at −800° C. for 1–3 days.

Immunoprecilitation/Immunoblotting Neonatal rat serum proteins (500 Ag) were immunoprecipitated in 1 ml of 50 mM Hepes buffer (pH7.4) containing 0.15 M NaCl, 0.05% Triton X-100 and the protease inhibitors using a rabbit polyclonal antibody against the rat M6P/IGF-II receptor (provided by Drs. R. G. MacDonald & C. D. Scott). The protein mixture was incubated overnight at 4° C. under constant rotation. The antibody-M6P/IGF-IIR complexes were adsorbed with 30 µl protein G-agarose (Santa Cruz Biotechnology). After a further 2 hour incubation with rotation at 4° C., the samples were centrifuged and the pellets were washed 3 times with ice cold PBS buffer (pH 7.4). The proteins were finally solubilized from the pellet with SDS/PAGE loading solution by incubation at 100° C. for 5 min.

The samples were analysed by SDS/PAGE and fluorography, as described above. For immunoblotting, proteins were seperated by SDS-PAGE under reducing or nonreducing conditions (ref. 23 & see FIG. 3) and then electrophoretically transferred onto Immobilon-P Transfer Membrane (Millipore). The blots were blocked with 5% nonfat milk, incubated with anti-IGF-II receptor antibodies and washed. The immunoreaction was visualized using the peroxidase-chemilunescence system.

Affinity Chromatography Phosphomannan was prepared by the method of Bretthauer et al. (*Biochemistry* 12:1251–1256). A phosphomannan-Sepharose affinity column was made according to the method of Sahagian et al. (*Meth. Enzymol*. 83:392-396). Affinity chromatography was performed essentially as described by Valenzano et al. (*J. Biol. Chem*. 270:16441-16448). Fresh neonatal rat serum was used after being diluted with PBS containing protease inhibitor mixture (as decribed above) and filtered through a 0.2 μM cellulose acetate membrane (Millipore).

Ligand-Binding Assay Assay of [³H]RA binding to M6P/IGF2R protein was performed according to the method of Sablonniere et al., 1994, *Anal. Biochem*. 217:110–118. Partially purified M6P/IGF-II receptors from neonatal rat serum was prepared using a Fast Protein Liquid Chromatography (FPLC) system equipped with a Sepharose-12 column (Pharmacia). The partially purified M6P/IGF2R protein was diluted in binding buffer (20 mM Tris-HCl, pH 8.0/150 mM NaCl/1mM DTT/protease inhibitors) at a concentration of 50 Ag/ml. Various amounts of tritiated and unlabeled RA in ethanol were added to incubation tubes and evaporated under nitrogen, and 200 μl diluted protein solution was immediately added. Incubation was carried out at 22° C. for 2 h in the dark. After the incubation, 0.2 ml chilled charcoal-dextran suspension (charcoal/dextran/glycerol=0.5%/0.05%/20%) was added to remove the unbound ligand. The bound [³H]RA in the supernatant was counted for radioactivity. Nonspecific binding was usually measured in the presence of a 200-fold excess of nonradioactive RA.

β-glucuronidase Binding and Endocytosis For binding assays, cells were permeabilized with saponin, incubated with β-glucuronidase (20,000 units/ml) with or without 1 μM RA for 3 h on ice, washed, solubilized and assayed for β-glucuronidase essentially as described by Miniti et al., 1992, *J. Biol. Chem*. 267:9000–9004. Specific enzyme binding was calculated by subtracting nonspecific binding (in the presence of 10 mM M6P) from total binding. Under these conditions (pH7.5), the cation-dependent 46-kDa receptor did not contribute to enzyme binding.

Endocytosis of extracellular β-glucuronidase was determined as described by Kyle et al., 1988, *J. Biol. Chem*. 263:16230–16235. Cultured neonatal rat cardiac myocytes were washed three times with MEM medium and incubated for 2 h at 37° C. with 1 ml of MEM containing 10,000 units of human β-glucuronidase, and with or without 5 mM mannose 6-phosphate, in the presence or absence of 2 μM RA. Following the incubation, the-cells were washed five times with ice-cold PBS, pH 7.4, and solubilized in 0.5% sodium deoxycholate. Detergent-solubilized extract is assayed for human β-glucuronidase activity-as described above.

Intracellular Trafficking Materials Retinoic acid was obtained from Sigma Chem. Co. (St. Louis, Mo.). The synthetic retinoids used (AGN193109, TTNPB) were produced by Allergan Inc. (Irvine, Calif.). Stably-transfected P388D1 cells re-expressing the M6P/IGF2R were provided by Dr. William S. Sly (St. Louis University). The rabbit polyclonal antibody against the rat M6P/IGF-II receptor was a gift from Dr. R.G. MacDonald (University of Nebraska). The rabbit polyclonal anti-rat cathepsin B antibody was purchased from Upstate Biotechnology (N.Y.). The FITC-conjugated goat anti-rabbit IgG was obtained from Jackson ImmunoResearch Laboratories (West Grove, Pa.). Neonatal rat cardiac fibroblasts were prepared from 1-day-old rats using the Neonatal Cardiomyocyte Isolation System (Worthington) and grown on glass coverslips in F-10 nutrient mixture with 10% horse serum and 5% fetal bovine serum (FBS). Cells were used in experiments after 3–5 days of culture. Mouse macrophage P3,88D1 cells were cultured in minimum essential medium-a (MEM-α) supplemented with 10% FBS.

Immunofluorescence Cells grown on glass coverslips for 3 days were treated with RA (0.25-1 μM) and/or synthetic retinoids for 2–3 h. Cells were then fixed with 4% paraformaldehyde in phosphate-buffered saline (PBS) for 30 min. The cells were washed in PBS, permeabilized with 0.1% Triton X-100 in PBS for 5 min, and then incubated with either polyclonal anti-rat M6P/IGF2R antibody or anti-rat cathepsin B antibody (diluted 1:200) at room temperature for 1 h. This was followed by washing in PBS and incubation with FITC-conjugated goat anti-rabbit IgG for 1 h at RT. After washing in PBS, the cells were mounted on glass slides in an anti-fade mounting medium and photographed with a Nikon photomicroscope.

Other embodiments are within the following claims.

We claim:

1. An in vitro method for inhibiting proliferation of a cell or inducing apoptosis, comprising:
   expressing M6P/IGF2R protein in the cell by introducing into the cell an expression vector comprising a polynucleotide encoding M6P/IGF2R protein; and
   contacting the cell with a compound that binds to the M6P/IGF2R protein, wherein the compound is a retinoid,
   thereby inhibiting proliferation of the cell or inducing apoptosis.

2. The method of claim 1, wherein the retinoid is selected from the group consisting of retinoic acid, 13-cis-retinoic acid, 9-cis-retinoic acid, retinol, and retinol acetate.

3. The method of claim 1, wherein the cell is a cancer cell.

4. The method of claim 1, wherein the cell is a mammalian cell.

5. The method of claim 1, wherein the compound binds to repeat 15 of the M6P/IGF2R protein.

6. The method of claim 5, wherein the compound binds to a site on the M6P/IGF2R protein that comprises amino acids 2213 to 2258 of SEQ ID NO:1.

7. A screening method for identification of compounds that bind directly to the retinoic acid binding site of a M6P/IGF2R protein, comprising:
   providing purified M6P/IGF2R protein possessing a retinoic acid binding site;

contacting the M6P/IGF2R protein with a candidate compound; and detecting binding of the candidate compound to the retinoic acid binding site of the M6P/IGF2R protein.

8. The method of claim 7, wherein the M6P/IGF2R protein is immobilized during the contacting step.

9. The method of claim 8, wherein the M6P/IGF2R protein is immobilized on an affinity chromatography column during the contacting step.

10. The method of claim 7, wherein the candidate compound is a retinoid.

11. The method of claim 7, wherein the binding is detected by a radioactive label.

12. The method of claim 7, wherein the binding is detected by competitive inhibition.

13. The method of claim 7, further comprising providing purified M6P/IGF2R protein lacking a retinoic acid binding site;

contacting the M6P/IGF2R protein lacking a retinoic acid binding site with a candidate compound;

detecting binding of the candidate compound to the M6P/IGF2R protein lacking a retinoic acid binding site; and comparing the binding of the candidate compound to the M6P/IGF2R protein lacking a retinoic acid binding site with the binding of the candidate compound to the M6P/IGF2R protein possessing a retinoic acid binding site.

14. An in vitro method for identification of compounds that bind directly to the retinoic acid binding site of a M6P/IGF2R protein, comprising:

providing a test cell expressing M6P/IGF2R protein;

contacting the test cell with a candidate compound; and detecting a response selected from the group consisting of: (a) enhancement in M6P/IGF2R protein trafficking in the cell, (b) increased binding of M6P/IGF2R protein to mannose-6-phosphate, and (c) increased endocytosis of lysosomal enzymes as an indication the candidate compound binds to the retinoic acid binding site of the M6P/IGF2R protein.

15. The method of claim 14, wherein the M6P/IGF2R protein-mediated anamal is binding of M6P/IGF2R protein to mannose-6-phosphate or endocytosis of lysosomal enzymes.

16. The method of claim 14, further comprising determining whether the candidate compound binds to M6P/IGF2R protein.

17. The method of claim 16, wherein determining whether the candidate compound binds to M6P/IGF2R protein comprises testing the effect of the candidate compound on a cell line that does not express M6P/IGF2R.

18. The method of claim 16, wherein determining whether the candidate compound binds to M6P/IGF2R protein comprises providing purified M6P/IGF2R protein;

contacting the purified M6P/IGF2R protein with a candidate compound; and detecting binding of the candidate compound to the purified M6P/IGF2R protein.

19. An in vitro method for inhibiting proliferation of a cell or inducing apoptosis, the method comprising:

identifying a cell as expressing an M6P/IGF2R protein; and contacting the cell with a retinoid that binds to an M6P/IGF2R protein, thereby inhibiting proliferation of the cell or inducing apoptosis.

20. The method of claim 19, wherein the retinoid is selected from the group consisting of retinoic acid, 13-cis-retinoic acid, 9-cis-retinoic acid, retinol, and retinol acetate.

21. The method of claim 19, wherein the cell is a mammalian cell.

22. The method of claim 19, wherein the cell is a cancer cell.

23. The method of claim 19, wherein the retinoid binds to repeat 15 of the M6P/IGF2R protein.

24. The method of claim 19, wherein the retinoid binds to a site on the M6P/IGF2R protein that comprises amino acids 2213 to 2258 of SEQ ID NO:1.

* * * * *